(12) United States Patent
Hikita et al.

(10) Patent No.: US 10,129,463 B2
(45) Date of Patent: Nov. 13, 2018

(54) IMAGE PROCESSING APPARATUS FOR ELECTRONIC ENDOSCOPE, ELECTRONIC ENDOSCOPE SYSTEM, AND IMAGE PROCESSING METHOD FOR ELECTRONIC ENDOSCOPE

(71) Applicant: FUJIFILM Corporation, Tokyo (JP)

(72) Inventors: Mai Hikita, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 330 days.

(21) Appl. No.: 14/868,404

(22) Filed: Sep. 29, 2015

(65) Prior Publication Data

US 2016/0105606 A1 Apr. 14, 2016

(30) Foreign Application Priority Data

Oct. 9, 2014 (JP) .................................. 2014-207799

(51) Int. Cl.
| | | |
|---|---|---|
| *A61B 1/00* | (2006.01) | |
| *H04N 5/232* | (2006.01) | |
| *H04N 5/225* | (2006.01) | |
| *A61B 1/04* | (2006.01) | |
| *A61B 1/06* | (2006.01) | |

(52) U.S. Cl.
CPC ..... *H04N 5/23229* (2013.01); *A61B 1/00009* (2013.01); *A61B 1/00045* (2013.01); *H04N 5/2256* (2013.01); *H04N 5/23293* (2013.01); *H04N 5/23296* (2013.01); *A61B 1/0002* (2013.01); *A61B 1/041* (2013.01); *A61B 1/0684* (2013.01); *H04N 2005/2255* (2013.01)

(58) Field of Classification Search
CPC ............................................ G09G 2340/0442

USPC ............................................................ 348/65
See application file for complete search history.

(56) References Cited

U.S. PATENT DOCUMENTS

| | | | |
|---|---|---|---|
| 8,647,260 B2 | 2/2014 | Kamo | |
| 9,554,097 B2 | 1/2017 | Sasaki et al. | |
| 2012/0013798 A1* | 1/2012 | Arora | G06T 3/40 |
| | | | 348/445 |

FOREIGN PATENT DOCUMENTS

| | | |
|---|---|---|
| JP | H10336633 | 12/1998 |
| JP | 2009276371 | 11/2009 |

(Continued)

OTHER PUBLICATIONS

"Office Action of Japan Counterpart Application," dated Nov. 8, 2017, with English translation thereof, p. 1-p. 9, in which the listed references were cited.

*Primary Examiner* — Jeffery Williams
(74) *Attorney, Agent, or Firm* — JCIPRNET

(57) ABSTRACT

In the case where a value of the aspect ratio of the display area of an image display device is larger than a value of the aspect ratio of a captured image indicated by an imaging signal, image processing for making the magnification of an image of a peripheral portion outside a central portion of the captured image larger than the magnification of an image of the central portion so as to match the aspect ratio of the display area of the image display device is performed. Accordingly, the magnification of the image of the peripheral portion of the captured image is increased by using the display area that is elongated in the horizontal direction, without degrading the visibility of the image of the central portion of the captured image. As a result, it is possible to improve the visibility of the image of the peripheral portion.

20 Claims, 10 Drawing Sheets

(56) References Cited

FOREIGN PATENT DOCUMENTS

| | | | | |
|---|---|---|---|---|
| JP | 2011131023 A | * | 7/2011 | ......... A61B 1/00009 |
| JP | 2013066646 | | 4/2013 | |

* cited by examiner

[IMAGE DISPLAY DEVICE]

| NAME | NUMBER OF PIXELS (HORIZONTAL × VERTICAL) | ASPECT RATIO (HORIZONTAL :VERTICAL) | VALUE OF ASPECT RATIO (HORIZONTAL /VERTICAL) |
|---|---|---|---|
| VGA (Video Graphics Array) | 640 × 480 | 4:3 | 1.33 |
| XGA (Extended Graphics Array) | 1024 × 768 | 4:3 | 1.33 |
| SXGA (Super-XGA) | 1280 × 1024 | 5:4 | 1.25 |
| FHD (Full-High Definition) | 1920 × 1080 | 16:9 | 1.78 |
| WQXGA (Wide-Quad-XGA) | 2560 × 1600 | 8:5 | 1.6 |
| GHD (Quad-HD) | 2160 × 1440 | 3:2 | 1.5 |

4:3

IMAGE PROCESSING APPARATUS FOR ELECTRONIC ENDOSCOPE, ELECTRONIC ENDOSCOPE SYSTEM, AND IMAGE PROCESSING METHOD FOR ELECTRONIC ENDOSCOPE

CROSS-REFERENCE TO RELATED APPLICATIONS

The present application claims priority under 35 U.S.C. § 119 to Japanese Patent Application No. 2014-207799, filed on Oct. 9, 2014. The above application(s) is hereby expressly incorporated by reference, in its entirety, into the present application.

BACKGROUND OF THE INVENTION

1. Field of the Invention

The present invention relates to an image processing apparatus for an electronic endoscope, an electronic endoscope system, and an image processing method for an electronic endoscope, and in particular, to a technique for acquiring a high-quality endoscope image having a desired viewing angle.

2. Description of the Related Art

In the medical field, medical diagnosis using an endoscope has been performed. For example, in an electronic endoscope called an electronic scope, an insertion unit to be inserted into the body of a patient is provided. An objective lens, a solid state imaging device that captures an optical image formed by the objective lens, and the like are provided in the inner space of an insertion unit tip portion that is a tip portion of the insertion unit.

In the case of an endoscope to observe the lumen, if there are folds or protrusions in the lumen, it is difficult to observe portions hidden in the folds or protrusions even if the endoscope tip is curved. Therefore, the field of view of the objective lens of the endoscope is set as a wide angle in order to extend the observation range. However, in the case of the wide-angle objective lens, distortion is likely to occur. Accordingly, there is a problem that an image near the field of view appears to be distorted.

On the other hand, an endoscope image apparatus has been proposed that allows easier viewing especially in a peripheral portion of the screen while taking into consideration the observation angle of view and the size of the optical system (JP2009-276371A).

In the endoscope image apparatus disclosed in JP2009-276371A, when moving and transforming the position of an optical image formed on the imaging device, the electronic magnification of an image is operated independently in the radiation direction and the concentric direction. As a result, distortion is corrected so that the peripheral portion can be seen more clearly than the central portion.

SUMMARY OF THE INVENTION

In the endoscope image apparatus disclosed in JP2009-276371A, an electronic magnification in the radiation direction of a peripheral portion of a captured image is made to be larger than that in the concentric direction of the peripheral portion, so that the peripheral portion can be seen more clearly than the central portion. However, as a result of making the electronic magnification of the peripheral portion larger than that of the central portion, there is a problem that the visibility of the central portion is degraded.

That is, in the case where the electronic magnification of the peripheral portion is made to be larger than that of the central portion, the image of the central portion is relatively reduced in size, compared with a case in which the electronic magnification of the peripheral portion and the electronic magnification of the central portion are not changed. As a result, the visibility of the central portion is degraded.

The invention has been made in view of such a situation, and it is an object of the invention to provide an image processing apparatus for an electronic endoscope, an electronic endoscope system, and an image processing method for an electronic endoscope that can improve the visibility of an image of a peripheral portion of a captured image under certain conditions without degrading the visibility of an image of a central portion of the captured image that is captured by a wide-angle objective lens.

In order to achieve the above-described object, an image processing apparatus for an electronic endoscope according to an aspect of the invention includes: an input unit to which an imaging signal captured by an electronic endoscope is input; an image processing unit that performs image processing on the imaging signal input from the input unit; an image display device that images an imaging signal, which has been subjected to the image processing by the image processing unit; and an output unit that outputs an imaging signal, which has been subjected to the image processing by the image processing unit, to the image display device. The image processing unit performs first image processing in the case where a value of an aspect ratio of a display area of the image display device is larger than a value of an aspect ratio of a captured image indicated by the imaging signal, and performs second image processing in the case where the value of the aspect ratio of the display area of the image display device is equal to or less than the value of the aspect ratio of the captured image indicated by the imaging signal. The first image processing is for making a magnification of an image of a peripheral portion outside a central portion of the captured image larger than a magnification of an image of the central portion so as to match the aspect ratio of the display area of the image display device, and the second image processing is for fixing a magnification of an entire area of the captured image so as to match the aspect ratio of the display area of the image display device.

According to the aspect of the invention, in the case where the value of the aspect ratio of the display area of the image display device is larger than the value of the aspect ratio of the captured image indicated by the imaging signal, the first image processing for making the magnification of the image of the peripheral portion of the captured image larger than the magnification of the image of the central portion of the captured image so as to match the aspect ratio of the display area of the image display device is performed. Therefore, the visibility of the image of the central portion of the captured image is not degraded. In addition, in the case where the value of the aspect ratio of the display area of the image display device is larger than the value of the aspect ratio of the captured image (that is, in the case of an image display device that is horizontally long relative to an image display device having the same aspect ratio as the aspect ratio of the captured image), the magnification of the image of the peripheral portion of the captured image is increased by using a display area that is elongated in the horizontal direction. Therefore, it is possible to improve the visibility of the image of the peripheral portion. In addition, in the case where the value of the aspect ratio of the display area of the image display device is equal to or less than the value of the aspect ratio of the captured image indicated by the imaging signal, the second image processing for fixing the magnification of the entire area of the captured image so as to match the aspect ratio of the display area of the image display device is performed. Therefore, the visibility of the image of the central portion of the captured image is not degraded.

In the image processing apparatus for an electronic endoscope according to the aspect of the invention, it is preferable to further include a lens information acquisition unit that acquires lens information indicating lens characteristics of an objective lens from the electronic endoscope through communication with the electronic endoscope. In addition, it is preferable that the image processing unit performs only the second image processing in the case where it is determined that a maximum angle of view of the objective lens of the electronic endoscope is less than 120° based on the lens information acquired by the lens information acquisition unit.

In the case where the maximum angle of view of the objective lens is less than 120°, the peripheral portion of the captured image is not greatly compressed. Accordingly, even if the second image processing for fixing the magnification of the entire area of the captured image is performed, it is possible to ensure the visibility of the peripheral portion.

In the image processing apparatus for an electronic endoscope according to the aspect of the invention, it is preferable to further include a lens information acquisition unit that acquires lens information indicating lens characteristics of an objective lens from the electronic endoscope through communication with the electronic endoscope. In addition, preferably, in the case where the value of the aspect ratio of the display area of the image display device is larger than the value of the aspect ratio of the captured image indicated by the imaging signal and the objective lens of the electronic endoscope is determined to be a wide-angle lens, which has a maximum angle of view of 120° or more and which forms an image by compressing an angle of view according to an increase in an image height of the captured image, based on the lens information acquired by the lens information acquisition unit, the image processing unit makes the magnification of the image of the peripheral portion larger than the magnification of the image of the central portion by setting the image having a compressed angle of view as the image of the peripheral portion.

Although the objective lens that is a wide-angle lens having a maximum angle of view of 120° or more forms an image by compressing the angle of view according to an increase in the image height of the captured image, the visibility of the peripheral portion is improved by making the magnification of the image (image of the peripheral portion) having an angle of view compressed as described above larger than the magnification of the image of the central portion.

In the image processing apparatus for an electronic endoscope according to the aspect of the invention, it is preferable to further include a lens information acquisition unit that acquires lens information indicating lens characteristics of an objective lens from the electronic endoscope through communication with the electronic endoscope. In addition, preferably, in the case where making the magnification of the image of the peripheral portion of the captured image larger than the magnification of the image of the central portion, the image processing unit specifies the image of the central portion and the image of the peripheral portion of the captured image based on the lens information acquired by the lens information acquisition unit.

Therefore, since it is possible to specify the image of the central portion and the image of the peripheral portion of the captured image based on the lens information indicating the lens characteristics of the objective lens, it is possible to specify the central portion and the peripheral portion having different magnifications in the case where performing the first image processing. In particular, in the case where the lens characteristics of the objective lens differ depending on an electronic endoscope, it is possible to perform the first image processing with appropriate magnification for the central portion and the peripheral portion of the captured image.

In the image processing apparatus for an electronic endoscope according to the aspect of the invention, it is preferable to further include a magnification setting unit that arbitrarily sets the magnification of each of the central portion and the peripheral portion of the captured image in the first image processing of the image processing unit.

In the image processing apparatus for an electronic endoscope according to the aspect of the invention, it is preferable to further include a display size acquisition unit that acquires a display size of a display area of the image processing apparatus through communication with the image display device. In addition, preferably, the magnification setting unit sets the magnification of each of the central portion and the peripheral portion of the captured image based on the display size of the display area of the image processing apparatus acquired by the display size acquisition unit and a set display size of the central portion of the captured image by arbitrarily setting the display size of the central portion of the captured image. If the display size of the display area of the image processing apparatus and the display size of the central portion of the captured image are determined, the display size of the peripheral portion is determined. As a result, it is possible to set the magnification of each of the central portion and the peripheral portion of the captured image.

In the image processing apparatus for an electronic endoscope according to the aspect of the invention, it is preferable to further include a display size acquisition unit that acquires a display size of a display area of the image processing apparatus through communication with the image display device. In addition, preferably, the magnification setting unit sets the magnification of each of the central portion and the peripheral portion of the captured image based on the display size of the display area of the image processing apparatus acquired by the display size acquisition unit and a set display size of the peripheral portion of the captured image by arbitrarily setting the display size of the peripheral portion of the captured image. If the display size of the display area of the image processing apparatus and the display size of the peripheral portion of the captured image are determined, the display size of the central portion is determined. As a result, it is possible to set the magnification of each of the central portion and the peripheral portion of the captured image.

In the image processing apparatus for an electronic endoscope according to the aspect of the invention, it is preferable to further include an image information acquisition unit that acquires information regarding the aspect ratio of the captured image through communication with the electronic endoscope. The information regarding the aspect ratio of the captured image is the image size (the number of pixels in the horizontal direction×the number of pixels in the vertical direction) of the captured image or the ratio of the number of pixels of the captured image in the vertical direction to the number of pixels of the captured image in the horizontal direction.

In the image processing apparatus for an electronic endoscope according to the aspect of the invention, it is preferable to further include a display information acquisition unit that acquires information regarding the aspect ratio of the display area of the image display device through communication with the image display device. For example, in the case of communication with an image display device conforming to the high-definition multimedia interface standard (HDMI; registered trademark), it is possible to acquire display information, such as a display size, through the HDMI (registered trademark) terminal.

In the image processing apparatus for an electronic endoscope according to the aspect of the invention, it is preferable that the image processing unit performs the second image processing in the case where the display information acquisition unit cannot acquire the information regarding the aspect ratio of the display area of the image display device. This is to prevent the visibility of the central portion of the captured image from being degraded due to incorrect application of the first image processing.

In the image processing apparatus for an electronic endoscope according to the aspect of the invention, it is preferable to further include a mode selection unit that selects a first mode, in which the image processing unit performs the first image processing, or a second mode, in which the image processing unit performs the second image processing, by manual operation. In addition, preferably, the image processing unit performs the image processing by giving priority to the first image processing in the case where the first mode is selected by the mode selection unit, and performs the image processing by giving priority to the second image processing in the case where the second mode is selected by the mode selection unit. By giving priority to image processing corresponding to the mode selected by manual operation, it is possible to meet a demand to see an original image even if the image of the peripheral portion is compressed or a demand to give priority to the visibility of the peripheral portion even if the visibility of the central portion is degraded.

An electronic endoscope system according to another aspect of the invention includes: an electronic endoscope; the above-described image processing apparatus to which an imaging signal captured by the electronic endoscope is input; and an image display device to which the imaging signal after image processing from an output unit of the image processing apparatus is input.

An image processing method for an electronic endoscope according to still another aspect of the invention includes: a step of inputting an imaging signal captured by an electronic endoscope; a step of performing image processing on the input imaging signal; and a step of outputting an imaging signal after the image processing to an image display device. In the image processing step, first image processing is performed in the case where a value of an aspect ratio of a display area of the image display device is larger than a value of an aspect ratio of a captured image indicated by the imaging signal, and second image processing is performed in the case where the value of the aspect ratio of the display area of the image display device is equal to or less than the value of the aspect ratio of the captured image indicated by the imaging signal. The first image processing is for making a magnification of an image of a peripheral portion outside a central portion of the captured image larger than a magnification of an image of the central portion so as to match the aspect ratio of the display area of the image display device, and the second image processing is for fixing a magnification of an entire area of the captured image so as to match the aspect ratio of the display area of the image display device.

According to the invention, the magnification of the image of the peripheral portion of the captured image is made to be larger than the magnification of the image of the central portion of the captured image in the case where the value of the aspect ratio of the display area of the image display device is larger than the value of the aspect ratio of the captured image indicated by the imaging signal, and the magnification of the entire area of the captured image is fixed in the case where the value of the aspect ratio of the display area of the image display device is equal to or less than the value of the aspect ratio of the captured image indicated by the imaging signal. Therefore, the visibility of the image of the central portion of the captured image is not degraded regardless of the aspect ratio of the display area of the image display device and the aspect ratio of the captured image. In addition, since the magnification of the image of the peripheral portion of the captured image is made to be larger than the magnification of the image of the central portion of the captured image in the case where the value of the aspect ratio of the display area of the image display device is larger than the value of the aspect ratio of the captured image indicated by the imaging signal, it is possible to improve the visibility of the image of the peripheral portion of the captured image.

DESCRIPTION OF THE PREFERRED EMBODIMENTS

Hereinafter, an image processing apparatus for an electronic endoscope, an electronic endoscope system, and an image processing method for an electronic endoscope according to preferred embodiments of the invention will be described with reference to the accompanying diagrams.

[Overall Configuration of an Electronic Endoscope System]

Figure 1:
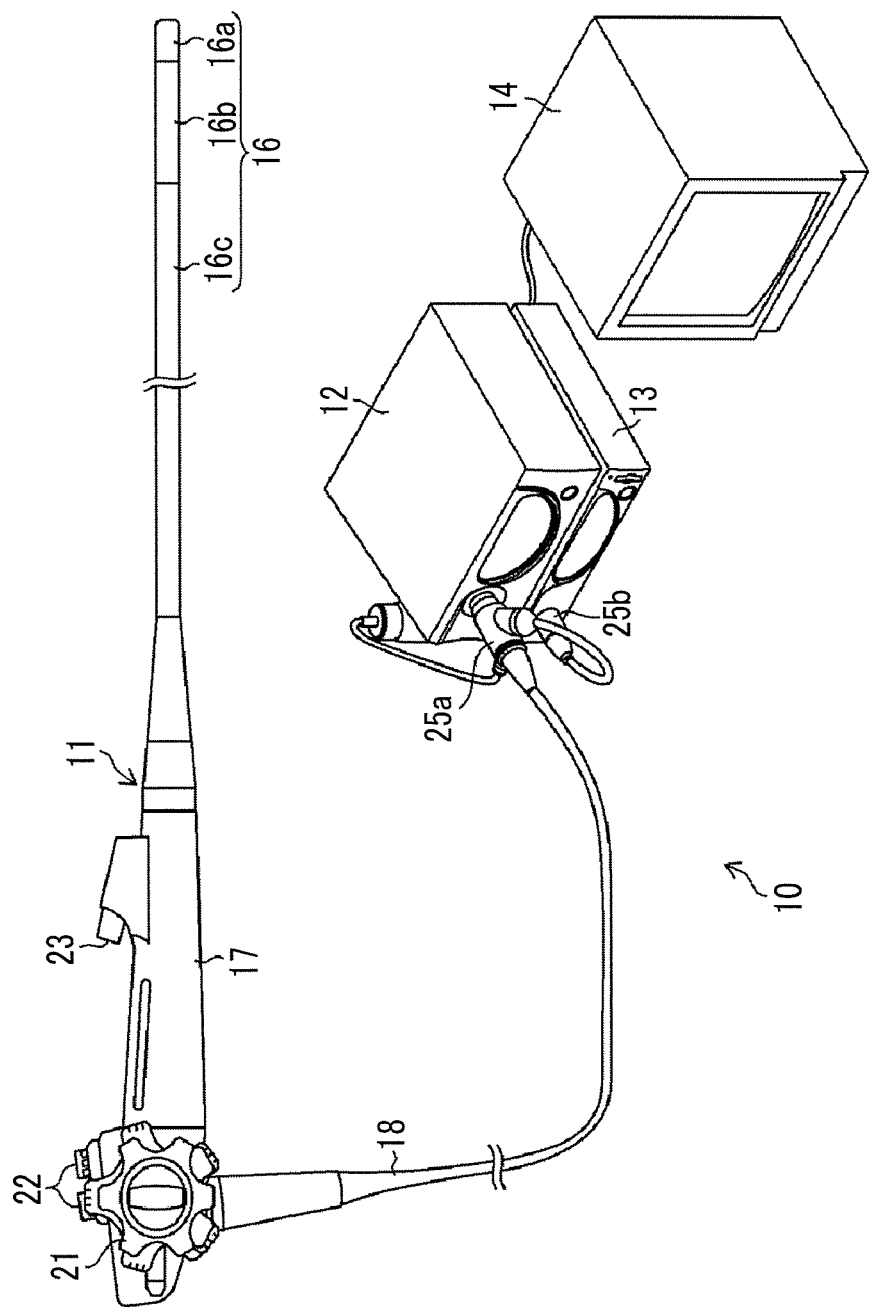
FIG. 1 is a perspective view of an electronic endoscope system according to the invention.

FIG. 1 is an external perspective view of an electronic endoscope system 10 according to the invention.

As shown in FIG. 1, the electronic endoscope system 10 mainly includes an electronic endoscope 11 as an electronic scope (here, a soft endoscope) that images an observation target inside the body of a patient, a light source device 12, a processor device 13, and an image display device (monitor) 14.

The light source device 12 supplies illumination light for illuminating the observation target to the electronic endoscope 11. The processor device 13 corresponds to one form of an image processing apparatus of the invention, and generates image data (hereinafter, referred to as "display image data") of a display image, which is displayed on the image display device 14, based on an image signal obtained by the electronic endoscope 11 and outputs the image data to the image display device 14. The image display device 14 displays an observation image of the observation target based on the image data input from the processor device 13.

The electronic endoscope 11 includes a flexible insertion unit 16 that is inserted into the body of a patient, a manual operation unit 17 that is provided continuously to a base portion of the insertion unit 16 and is used in order to grip the electronic endoscope 11 and operate the insertion unit 16, and a universal cord 18 for connecting the manual operation unit 17 to the light source device 12 and the processor device 13.

Figure 2:
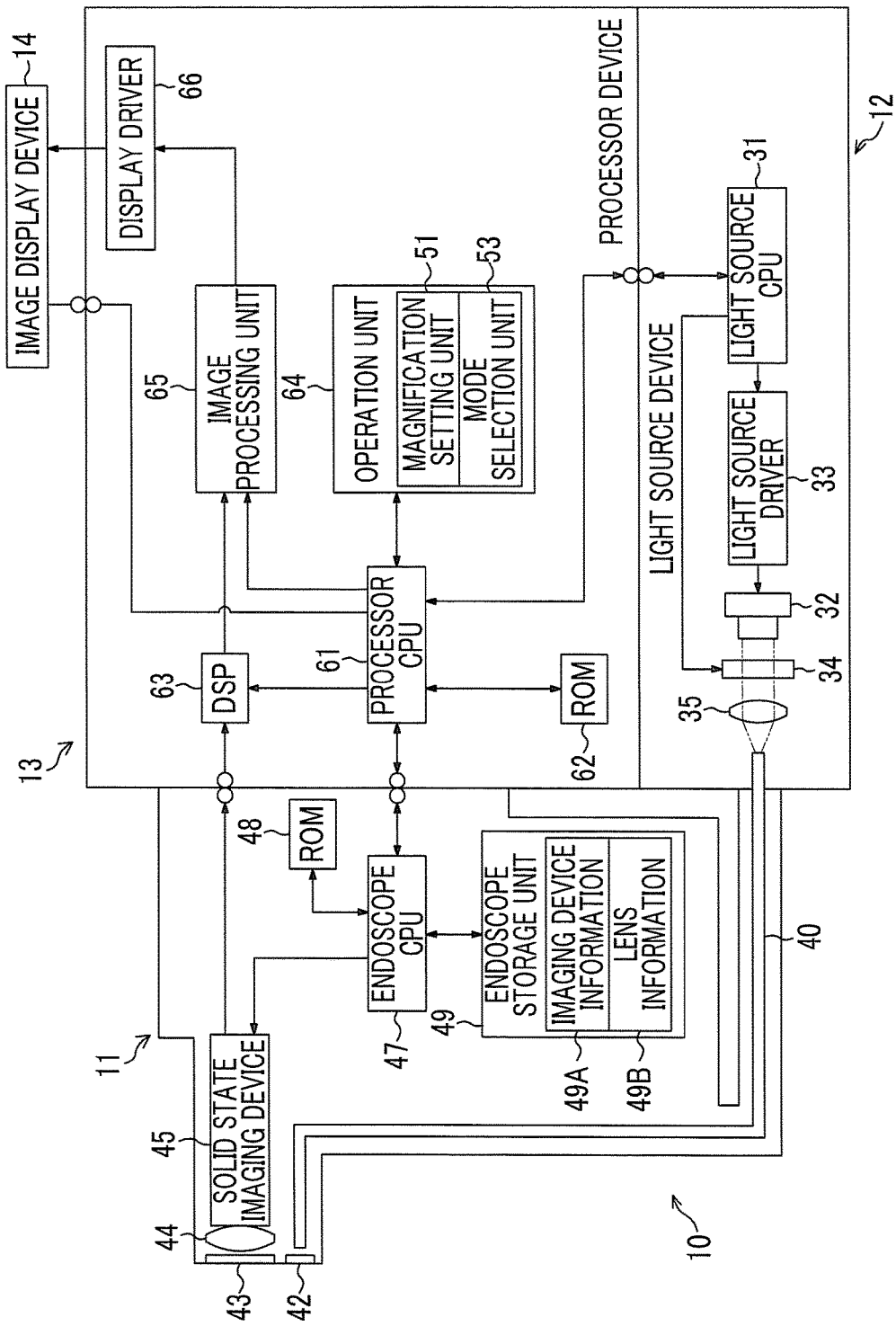
FIG. 2 is a block diagram showing the electrical configuration of the electronic endoscope system.

An illumination window 42 for illuminating the observation target, an objective lens 44 used for imaging, a solid state imaging device 45, and the like are provided in an insertion unit tip portion 16a that is a tip portion of the insertion unit 16 (refer to FIG. 2). A bending portion 16b that can bend is provided continuously to the rear end of the insertion unit tip portion 16a. In addition, a flexible tube portion 16c having flexibility is provided continuously to the rear end of the bending portion 16b.

An angle knob 21, operation buttons 22, a forceps inlet 23, and the like are provided in the manual operation unit 17. The angle knob 21 is rotated when adjusting the bending direction and the bending amount of the bending portion 16b. The operation buttons 22 are used for various operations, such as air supply, water supply, and suction. The forceps inlet 23 communicates with a forceps channel in the insertion unit 16.

Air and water supply channels, a signal cable, a light guide, and the like are included in the universal cord 18. A connector portion 25a connected to the light source device 12 and a connector portion 25b connected to the processor device 13 are provided in a tip portion of the universal cord 18. Therefore, illumination light is supplied from the light source device 12 to the electronic endoscope 11 through the connector portion 25a, and an image signal obtained by the electronic endoscope 11 is input to the processor device 13 through the connector portion 25b.

[Electrical Configuration of an Electronic Endoscope System]

FIG. 2 is a block diagram showing the electrical configuration of the electronic endoscope system 10. As shown in FIG. 2, the light source device 12 includes a light source central processing unit (light source CPU) 31, a light source 32, a light source driver 33, a diaphragm mechanism 34, and a condensing lens 35. The light source CPU 31 controls the light source driver 33 and the diaphragm mechanism 34. In addition, the light source CPU 31 performs communication with the processor CPU 61 of the processor device 13 in order to transmit and receive various kinds of information.

A xenon lamp, a semiconductor light source such as a light emitting diode (LED) or a laser diode (LD), and the like are used as the light source 32, and the emission of illumination light is controlled by the light source driver 33. The diaphragm mechanism 34 is disposed on the light emission side of the light source 32, and increases or decreases the amount of illumination light incident on the condensing lens 35 from the light source 32. The condensing lens 35 condenses illumination light passing through the diaphragm mechanism 34, and guides the illumination light to the incidence end of a light guide 40 in the connector portion 25a connected to the light source device 12.

The electronic endoscope 11 mainly includes the light guide 40, the illumination window 42, an observation window 43, the objective lens 44 and the solid state imaging device 45 that are one form of an imaging unit, an endoscope CPU 47, a read only memory (ROM) 48, and an endoscope storage unit 49.

As the light guide 40, a large-diameter optical fiber, a fiber bundle, and the like are used. The incidence end of the light guide 40 is inserted into the light source device 12 through the connector portion 25a, and the output end of the light guide 40 faces the illumination window 42 that is provided in the insertion unit tip portion 16a through the insertion unit 16. The illumination light supplied from the light source device 12 to the light guide 40 is emitted to the observation target through the illumination window 42. Then, the illumination light reflected or scattered by the observation target is incident on the objective lens 44 through the observation window 43.

The objective lens 44 is disposed on the back side of the observation window 43. The objective lens 44 forms the reflected light or scattered light of the illumination light incident through the observation window 43, that is, an optical image of the observation target, on the imaging surface of the solid state imaging device 45. In this example, the objective lens 44 is a wide-angle lens having a maximum angle of view (also referred to as a "viewing angle") of 120° or more. However, depending on the type, model, or the like of an electronic endoscope connected to the processor device 13, an objective lens having a maximum angle of view less than 120° may also be used.

The solid state imaging device 45 is a complementary metal oxide semiconductor (CMOS) type imaging device or a charge coupled device (CCD) type imaging device, and is relatively positioned and fixed to the objective lens 44 at a position on the back side of the objective lens 44. On the imaging surface of the solid state imaging device 45, a plurality of pixels formed by a plurality of photoelectric conversion elements (photodiodes) that photoelectrically convert an optical image are arranged in a two-dimensional manner. The solid state imaging device 45 converts the optical image formed by the objective lens 44 into an electrical image signal, and outputs the electrical image signal to the processor device 13.

When the solid state imaging device 45 is a CMOS type imaging device, an analog/digital (A/D) converter is built into the imaging device, and a digital image signal is directly output from the solid state imaging device 45 to the processor device 13. When the solid state imaging device 45 is a CCD type imaging device, the image signal output from the solid state imaging device 45 is converted into a digital image signal by an A/D converter (not shown) and is then output to the processor device 13.

The endoscope CPU 47 mainly controls the driving of the solid state imaging device 45 by sequentially executing various programs or data read from the ROM 48 or the like.

In addition, the endoscope CPU 47 transmits the information stored in the ROM 48 or the endoscope storage unit 49 to the processor device 13 through communication with the processor CPU 61 of the processor device 13. As the information transmitted to the processor device 13, for example, identification information for identifying the type of the electronic endoscope 11 is stored in the ROM 48.

Specifically, imaging device information 49A of the solid state imaging device 45 and lens information 49B of the objective lens 44, which will be described in detail later, are stored in advance, as the information transmitted to the processor device 13, in the endoscope storage unit 49 at the time of manufacture of the electronic endoscope 11.

The processor device 13 includes a processor CPU 61, a ROM 62, a digital signal processor (DSP) 63, an operation unit 64, an image processing unit 65, and a display driver 66.

The processor CPU 61 controls each unit of the processor device 13 by reading a required program or data from the ROM 62 and sequentially processing the program or the data.

In addition, the processor CPU 61 acquires identification information, the imaging device information 49A, and the lens information 49B through communication with the endoscope CPU 47, and outputs the acquired identification information to the DSP 63 and outputs the imaging device information 49A and the lens information 49B to the image processing unit 65. Therefore, the processor CPU 61 corresponds to one form of an image information acquisition unit and a lens information acquisition unit of the invention.

When the image display device 14 conforms to the high-definition multimedia interface standard (HDMI; registered trademark), the processor CPU 61 acquires display information, such as a display size, from the image display device 14 through the HDMI (registered trademark) terminal, and outputs the acquired display information to the image processing unit 65. Therefore, the processor CPU 61 corresponds to one form of a display size acquisition unit of the invention.

Figure 4:
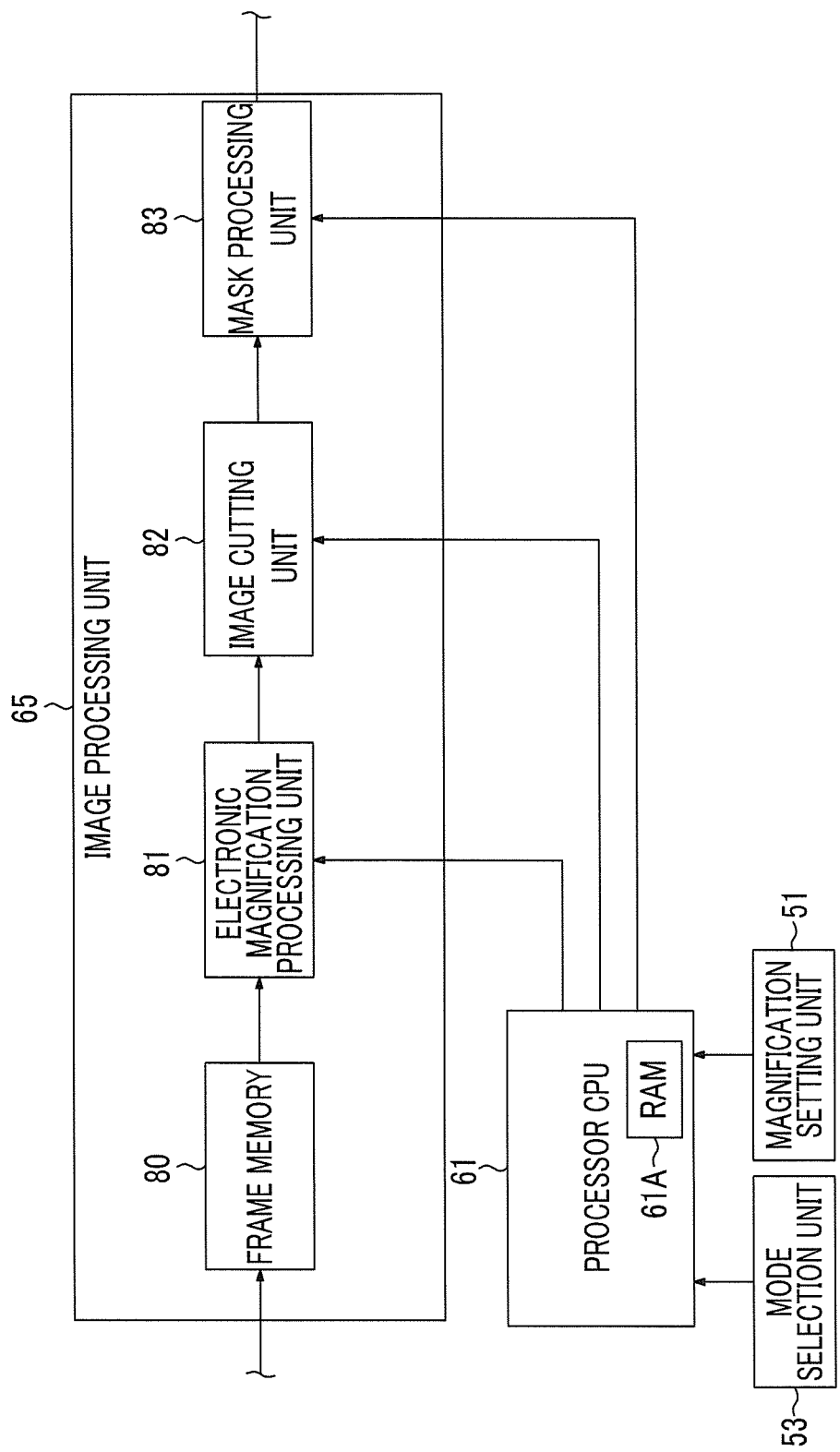
FIG. 4 is a diagram showing a case of cutting out an image corresponding to the display area relative to the center of the imaging area in a state in which the center of the displayable pixel area is shifted from the center of the imaging area.

The processor CPU 61 temporarily stores the imaging device information 49A and the lens information 49B acquired from the electronic endoscope 11 and the display information acquired from the image display device 14 in a built-in random access memory (RAM) 61A (FIG. 4).

The DSP 63 that functions as one form of an input unit to input an imaging signal output from the solid state imaging device 45 generates image data of one frame by performing various kinds of signal processing, such as color interpolation, color separation, color balance adjustment, gamma correction, and image enhancement processing, on the image signal of one frame input from the electronic endoscope 11 under the control of the processor CPU 61. In addition, the DSP 63 performs various kinds of signal processing corresponding to the type (model) of the electronic endoscope 11 based on the identification information input from the processor CPU 61. Then, the DSP 63 sequentially outputs the generated image data of one frame to the image processing unit 65.

The operation unit 64 corresponds to one form of a magnification setting unit 51 and a mode selection unit 53, which will be described in detail later.

As shown in FIG. 4, the image processing unit 65 includes an electronic magnification processing unit 81, an image cutting unit 82 that cuts out an image corresponding to the display area, and a mask processing unit 83 that covers a part of an image. The image processing unit 65 generates display image data by performing electronic magnification processing, image cutting processing, and mask processing on the image data input from the DSP 63, based on the imaging device information 49A and the lens information 49B acquired from the electronic endoscope 11 and the display information acquired from the image display device 14, under the control of the processor CPU 61. Then, the image processing unit 65 outputs the display image data to the display driver 66. Details of the image processing unit 65 will be described later.

The display driver 66 is an output unit that outputs the display image data to the image display device 14, and displays an observation image of an observation target on the image display device 14 based on the display image data input from the image processing unit 65.

Figure 3:
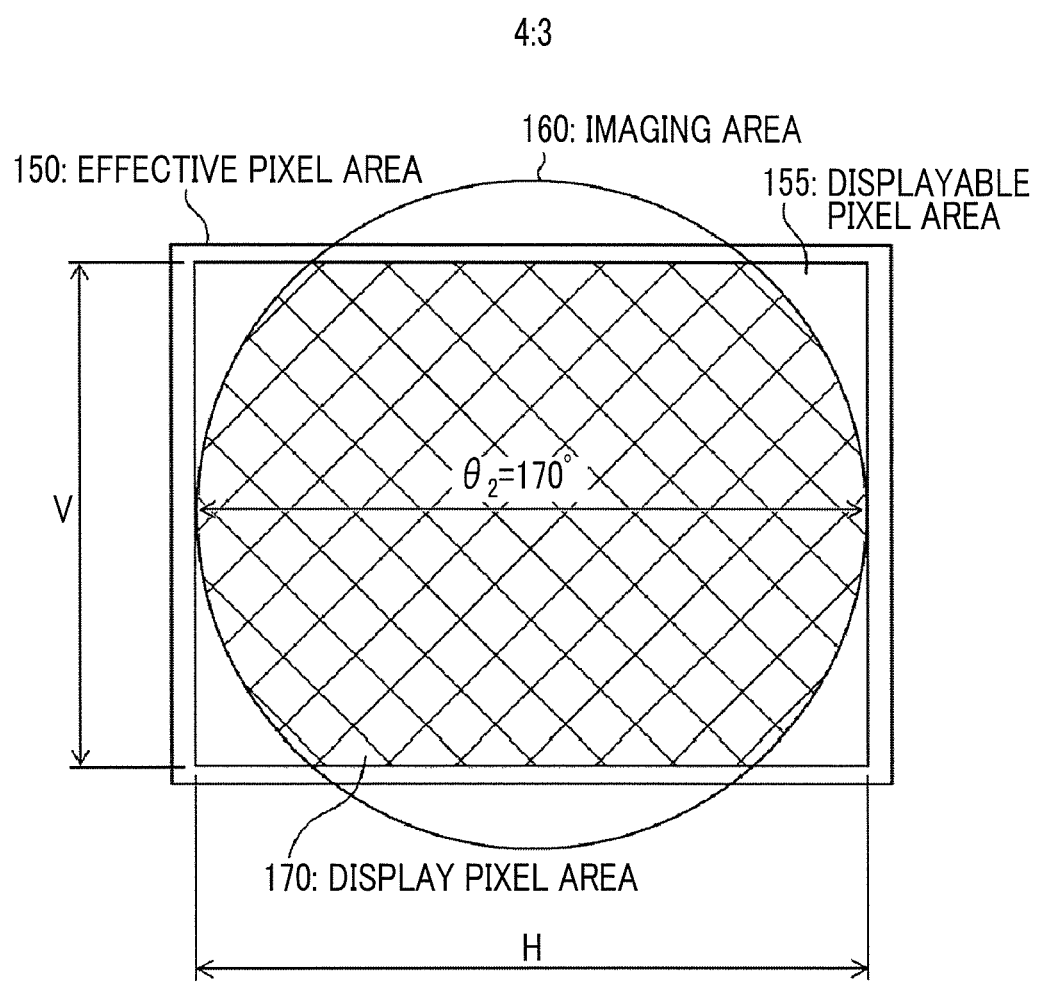
FIG. 3 is a diagram showing the positional relationship between an effective pixel area, a displayable pixel area, an imaging area where an optical image is formed by an objective lens, and a display pixel area displayed in the display area of an image display device, in a solid state imaging device.

FIG. 3 is a diagram showing the positional relationship between an effective pixel area 150, a displayable pixel area 155, an imaging area 160 where an optical image is formed by the objective lens 44, and a display pixel area 170 displayed in the display area of the image display device 14, in the solid state imaging device 45.

FIG. 3 shows a state in which the objective lens 44 and the solid state imaging device 45 are positioned with relatively high accuracy (ideally positioned state) so that the optical axis of the objective lens 44 matches the center of the displayable pixel area 155 of the solid state imaging device 45 and the optical axis direction is perpendicular to the surface of the displayable pixel area 155 (there is no inclination of the optical axis). In this example, the objective lens 44 is a wide-angle lens having a maximum angle of view ($\theta_2$) of 170°, and has lens characteristics of forming an image by largely compressing a peripheral portion outside a central portion (for example, a central portion having an angle of view less than 120°) of an imaging area 160 compared with the central portion.

In FIG. 3, the effective pixel area 150 is a pixel area where the signal of a pixel on the imaging surface of the solid state imaging device 45 is used as an actual imaging signal.

The displayable pixel area 155 that is an area that can be used for the image display in the image display device 14 is included in the effective pixel area 150. Specifically, the displayable pixel area 155 is an area excluding a portion to be used for image processing or the like and the margin of several pixels from the effective pixel area 150. The imaging signal read from the displayable pixel area 155 of the solid state imaging device 45 is a signal processed by the image processing unit 65.

In this example, the number of pixels (pixel size of a captured image showing an imaging signal) in the horizontal direction in the displayable pixel area 155 is H, and the number of pixels (pixel size of a captured image showing an imaging signal) in the vertical direction in the displayable pixel area 155 is V. The aspect ratio of a captured image that is an aspect ratio of the displayable pixel area 155 is 4:3 (=H:V).

The display pixel area 170 is an area corresponding to the observation target display area of an image displayed on the image display device 14. In this example, the display pixel area 170 is an overlapping area of the displayable pixel area 155 and the imaging area 160, and is an area that is cut out so as to match the aspect ratio of the display area of the image display device 14 when an aspect ratio, which is the aspect ratio of the display area of the image display device 14, and the aspect ratio of a captured image are not the same as will be described later (when the value of the aspect ratio of the display area of the image display device 14 is larger than the value of the aspect ratio of the captured image).

In addition, in this example, when the aspect ratio that is the aspect ratio of the display area of the image display device 14 is the same as the aspect ratio (4:3) of the captured image or when the value of the aspect ratio of the display area of the image display device 14 is smaller than the value of the aspect ratio of the captured image, image cutting processing for making the aspect ratios equal is not performed.

In addition, in this example, mask processing on the captured image (mask processing of covering a part of the image with a mask) is performed so as to obtain the same shape as the display area of the image display device 14. Therefore, when the aspect ratio of the display area of the image display device 14 is not the same as the aspect ratio of the captured image, it is possible to make both the aspect ratios equal by mask processing.

[Image Processing Unit]

FIG. 4 is a block diagram showing the internal configuration of the image processing unit 65 shown in FIG. 2.

As shown in FIG. 4, the image processing unit 65 mainly includes a frame memory 80, the electronic magnification processing unit 81, the image cutting unit 82, and the mask processing unit 83.

The imaging device information 49A and the lens information 49B acquired from the electronic endoscope 11 and the display information acquired from the image display device 14 are temporarily stored in the RAM 61A built into the processor CPU 61. The processor CPU 61 outputs control information indicating the processing content in the electronic magnification processing unit 81, the image cutting unit 82, and the mask processing unit 83 based on the information stored in the RAM 61A.

The frame memory 80 is a memory in which image data (image data of the displayable pixel area 155) of each one frame input from the DSP 63 is temporarily stored. Normally, image data of a plurality of frames is stored at the same time. In addition, new image data input from the DSP 63 is overwritten on the oldest image data stored in the frame memory 80.

The electronic magnification processing unit 81 generates display image data by electronically magnifying the image data at the input electronic magnification based on the control information indicating the electronic magnification that has been input from the processor CPU 61.

In this example, the electronic magnification processing is a process of increasing the number of pixels by interpolating the image data according to the electronic magnification so that the image size corresponding to the display area of the image display device 14 is obtained. Here, electronic magnification processing (first electronic magnification processing), in which the magnification of an image of a peripheral portion of image data (captured image) is made to be larger than the magnification of an image of a central portion, and electronic magnification processing (second electronic magnification processing) for fixing the magnification of the entire area of the image data (captured image) are performed.

Preferably, the number of pixels of the image size of image data (at least the number of pixels of image data in the horizontal direction or the vertical direction) after the electronic magnification processing of the electronic magnification processing unit 81 matches the number of pixels of the display area of the image display device 14. The processor CPU 61 can set the control information indicating the electronic magnification based on image size information of the solid state imaging device 45 included in the imaging device information 49A acquired from the electronic endoscope 11 and display size information included in the display information acquired from the image display device 14.

The electronic magnification processing unit 81 performs either the first electronic magnification processing or the second electronic magnification processing based on the control information input from the processor CPU 61. In addition, each area of the central portion and the peripheral portion of the captured image when performing the first electronic magnification processing and the electronic magnification of the image of the central portion and the electronic magnification of the image of the peripheral portion may be set in advance according to the image height of the captured image, or may be designated from the processor CPU 61.

Image data processed by the electronic magnification processing unit 81 and image cutting information from the processor CPU 61 are added to the image cutting unit 82. The image cutting unit 82 cuts out display image data from the input image data based on the input image cutting information, and outputs the cut display image data to the mask processing unit 83.

The image cutting information is information for making the aspect ratio of the input image data equal to the aspect ratio of the display area of the image display device 14. In this example, when the value of the aspect ratio of the display area of the image display device 14 is larger than the value of the aspect ratio of the captured image, image cutting information is output from the processor CPU 61. When the value of the aspect ratio of the display area of the image display device 14 is equal to or less than the value of the aspect ratio of the captured image, image cutting information is not output from the processor CPU 61. Accordingly, the image cutting unit 82 does not perform cutting processing on the image based on the input image data, and outputs the input image data to the mask processing unit 83 as it is.

The mask processing unit 83 performs mask processing for masking display image data in the same shape as the display area based on the mask image data, thereby generating display image data.

That is, the mask processing unit 83 performs the mask processing in a method in which pixels corresponding to the display area (pixels corresponding to a non-mask portion)

are output as they are based on mask image data set in advance and pixels corresponding to the outside of the display area (pixels corresponding to a mask portion) are discarded and mask pixels are output instead while inputting the display image data from the image cutting unit 82 by one pixel at a time. The mask image data is, for example, data in which the display area corresponding to the display pixel area 170 is colorless and transparent and the area (mask area) outside the display area corresponds to a low-brightness (black) pixel. There are various forms of mask image data. For example, there is an image that masks the four corners of the display image data or an image that masks the outside of a circle, of which upper and lower portions have been cut out, in display image data of the circle.

The mask processing unit 83 outputs the display image data after the mask processing to the display driver 66. Then, an observation image of the observation target based on the display image data is displayed on the image display device 14 by the display driver 66. In addition, the mask processing of the mask processing unit 83 is not indispensable image processing in the invention.

[Display Size of an Image Display Device]

Figures 5, 6:
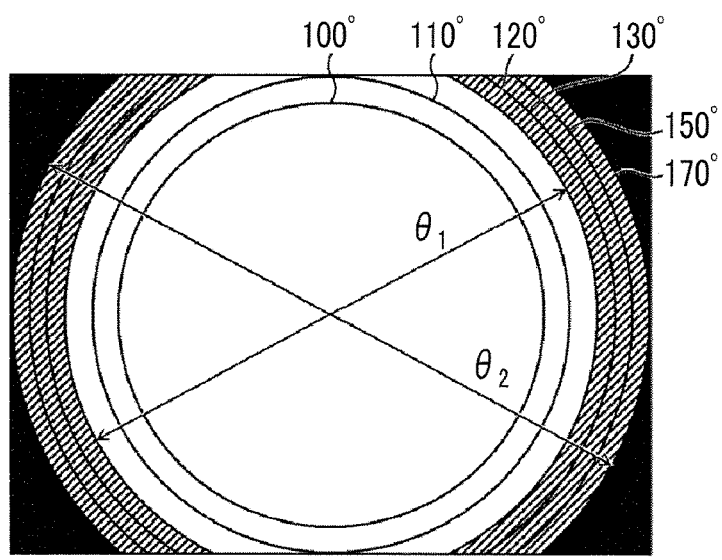
FIG. 5 is a table showing the display sizes of various kinds of image display devices.
FIG. 6 is a diagram showing an example of the display screen displayed on the image display device in the case where the aspect ratio of a captured image and the aspect ratio of the display area of the image display device are the same.

FIG. 5 is a graph showing the display sizes of various kinds of image display device.

As shown in FIG. 5, image display devices applied to the electronic endoscope system 10 have various display sizes (various numbers of pixels and aspect ratios). In addition, the types of the image display device shown in FIG. 5 are just examples.

On the other hand, the aspect ratio of a captured image that is captured by the solid state imaging device 45 of the electronic endoscope 11 is 4:3.

FIG. 5 shows the number of pixels (horizontal×vertical), an aspect ratio (horizontal:vertical), and a value (horizontal÷vertical) of the aspect ratio in various kinds of image display device.

In the invention, when the value of the aspect ratio of the display area of the image display device is larger than the value (=1.33) of the aspect ratio of a captured image, first image processing for making the magnification of an image of a peripheral portion of the captured image larger than the magnification of an image of a central portion of the captured image so as to match the aspect ratio of the display area of the image display device is performed. When the value of the aspect ratio of the display area of the image display device is equal to or less than the value of the aspect ratio of the captured image, second image processing for fixing the magnification of the entire area of the captured image so as to match the aspect ratio of the display area of the image display device is performed.

Preferably, the magnification of the image of the central portion in the first image processing is determined according to the ratio between the number of pixels in the vertical direction of the display area of the image display device and the number of pixels in the vertical direction of the captured image, and the magnification in the second image processing is determined according to the ratio between the number of pixels in the horizontal direction of the display area of the image display device and the number of pixels in the horizontal direction of the captured image.

The aspect ratio of the captured image output from the solid state imaging device 45 of the electronic endoscope 11 is generally 4:3, but the invention is not limited thereto.

[When the Aspect Ratios are the Same]

FIG. 6 is a diagram showing an example of a display screen that is displayed on the image display device 14 when the aspect ratio (4:3) of a captured image and the aspect ratio of the display area of the image display device 14 are the same. In the example shown in FIG. 5, in cases of an image display device having the number of pixels (640×480) of Video Graphics Array (VGA) and an image display device having the number of pixels (1280×768) of eXtended Graphics Array (XGA), the aspect ratio of the display area and the aspect ratio of the captured image in these image display devices are the same.

In this case, the electronic magnification processing unit 81 performs the second electronic magnification processing in which electronic magnification processing is performed with a fixed magnification for the entire area of the captured image based on the control information from the processor CPU 61, and the image cutting unit 82 outputs image data after the electronic magnification processing to the subsequent mask processing unit 83 as it is. Such image processing corresponds to second image processing of the invention.

The mask processing unit 83 performs mask processing on an unnecessary area in the display image data based on the mask image data.

That is, as is apparent from a comparison between each area of the solid state imaging device 45 shown in FIG. 3 and the display screen shown in FIG. 6, the image of the displayable pixel area 155 shown in FIG. 3 is subjected to the second electronic magnification processing by the electronic magnification processing unit 81, and an area outside the display area (in the example shown in FIG. 6, a maximum angle of view ($\theta_2$=170°)) of the image display device 14 corresponding to the display pixel area 170 is subjected to mask processing.

As shown in FIG. 6, assuming that an image within a predetermined angle of view ($\theta_1$=120°) in a captured image is an image of a central portion and an image between the angle of view ($\theta_1$=120°) and the maximum angle of view ($\theta_2$=170°) is an image (image indicated by oblique lines) of a peripheral portion, it can be seen that an image of the peripheral portion in the captured image is greatly compressed by the wide-angle objective lens 44 compared with the image of the central portion.

[When the Aspect Ratios are not the Same (when the Display Area has a Horizontally Long Aspect Ratio with Respect to a Captured Image)]

Figure 7:
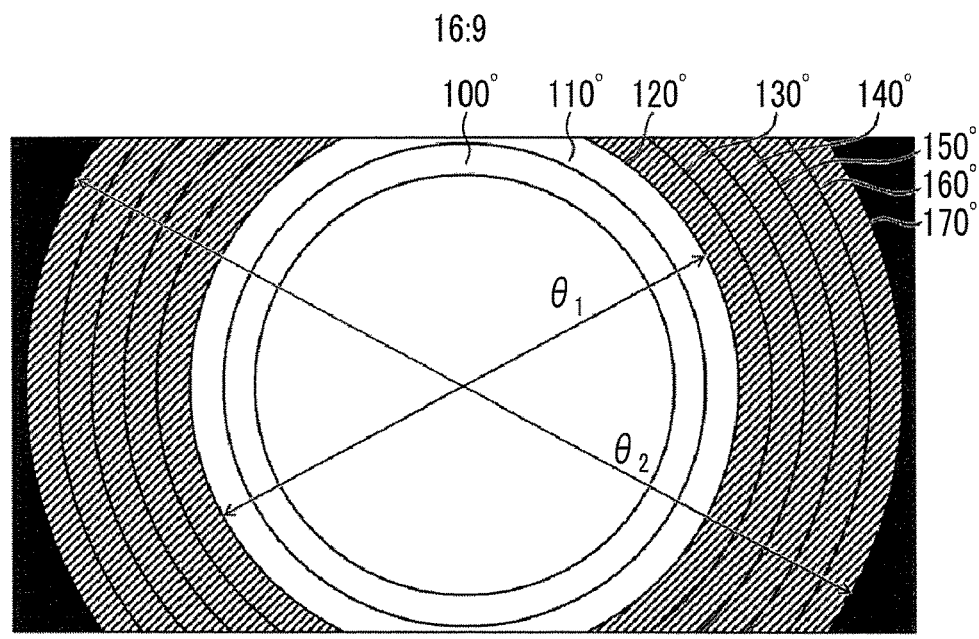
FIG. 7 is a diagram showing an example of the display screen displayed on the image display device in the case where the aspect ratio of a captured image is 4:3 and the aspect ratio of the display area of the image display device is 16:9.
Figure 8:
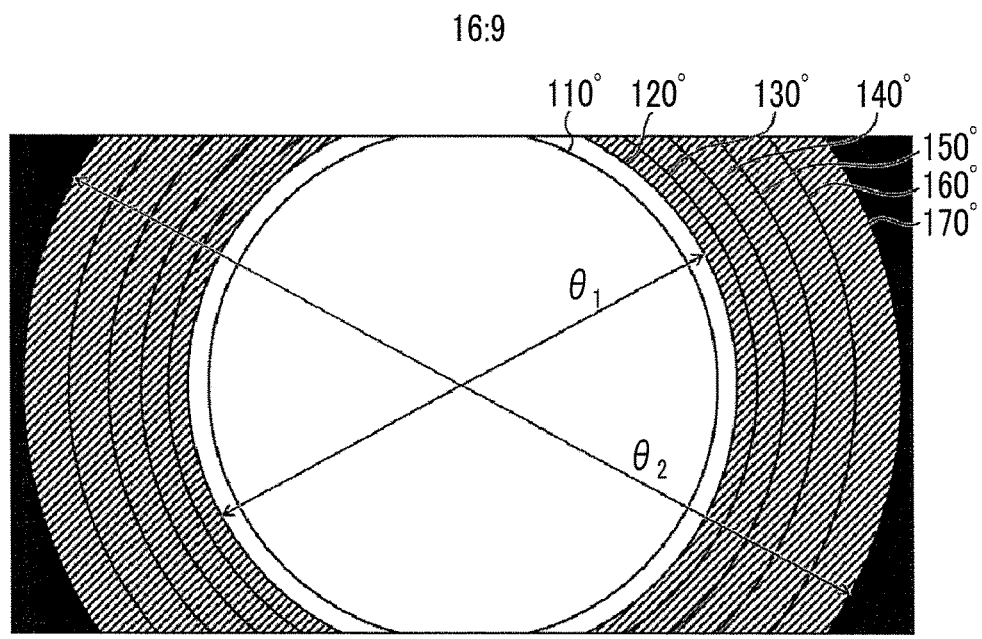
FIG. 8 is a diagram showing another example of the display screen displayed on the image display device in the case where the aspect ratio of a captured image is 4:3 and the aspect ratio of the display area of the image display device is 16:9.
Figure 9:
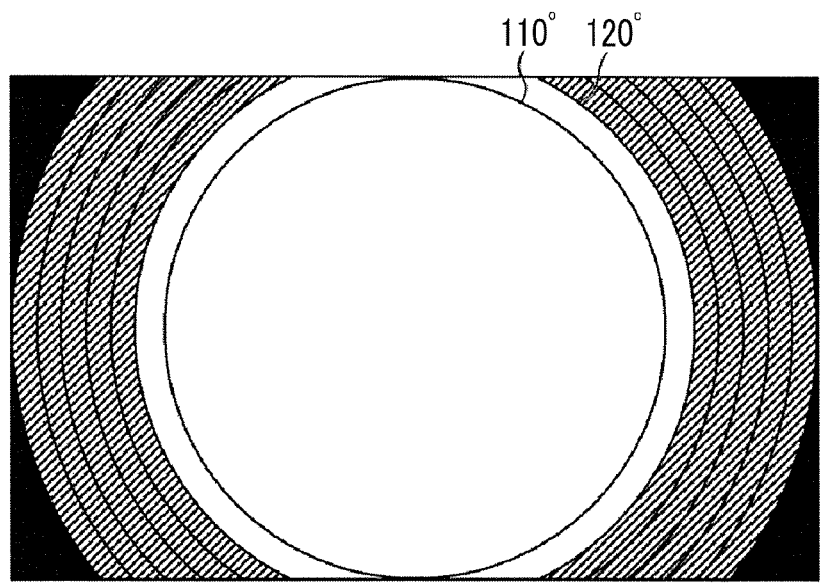
FIG. 9 is a diagram showing an example of the display screen displayed on the image display device in the case where the aspect ratio of a captured image is 4:3 and the aspect ratio of the display area of the image display device is 8:5.

FIGS. 7 to 9 are diagrams showing examples of a display screen that is displayed on the image display device 14 when the aspect ratio (4:3) of a captured image is not the same as the aspect ratio of the display area of the image display device 14. In particular, FIGS. 7 to 9 show a case in which the value of the aspect ratio of the display area of the image display device 14 is larger than the value of the aspect ratio of the captured image (case in which the display area has a horizontally long aspect ratio with respect to the captured image).

FIGS. 7 and 8 show a case in which the aspect ratio of the display area of the image display device 14 is 16:9, and the image display device of Full High Definition (HID) in the example shown in FIG. 5 corresponds to this case.

In the example shown in FIG. 7, the electronic magnification processing unit 81 performs the first electronic magnification processing by making the magnification of the image of the peripheral portion of the captured image larger than the magnification of the image of the central portion of the captured image based on the control information from the processor CPU 61. The image cutting unit 82 cuts out display image data from the image data that has been subjected to electronic magnification processing so that the same aspect ratio as the aspect ratio (16:9) of the display area of the image display device 14 is obtained, and outputs the cut display image data to the mask processing unit 83. Such image processing corresponds to first image processing of the invention.

The mask processing unit 83 performs mask processing on an unnecessary area in the display image data based on the mask image data.

Although the image of the peripheral portion in the captured image is greatly compressed by the wide-angle objective lens 44 compared with the image of the central portion, electronic magnification processing (first electronic magnification processing) for making the magnification of the image of the peripheral portion of the captured image larger than the magnification of the image of the central portion of the captured image is performed so that the visibility of the image of the peripheral portion is improved.

That is, as shown in FIG. 7, when displaying an image on the image display device 14 of a wide screen having an aspect ratio of 16:9, if the same image processing as the image processing (second image processing) shown in FIG. 6 is performed, a margin (masked area or the like) is generated on the left and right sides of the wide screen of the image display device 14. Accordingly, the wide screen cannot be effectively used. However, by performing the first electronic magnification processing for making the magnification of the image of the peripheral portion of the captured image larger than the magnification of the image of the central portion of the captured image as described above, the visibility of the image of the peripheral portion can be improved, and the wide screen of the image display device 14 can be effectively used.

In the first electronic magnification processing shown in FIG. 7, electronic magnification is performed so that the display width per unit angle of the image of the peripheral portion (angle of view: $\theta_1$ to $\theta_2$) of the captured image is approximately the same as the display width per unit angle of the central portion (in particular, a central portion in the vicinity of the angle of view $\theta_1$) of the captured image.

The embodiment shown in FIG. 8 is different from the embodiment shown in FIG. 7 in terms of the content of the first electronic magnification processing.

That is, in the first electronic magnification processing shown in FIG. 8, the magnification increases as the angle of view increases when making the magnification of the image (image indicated by oblique lines) of the peripheral portion of the captured image larger than the magnification of the image of the central portion of the captured image. That is, in the first electronic magnification processing shown in FIG. 8, electronic magnification is performed so that the display width per unit angle of the image of the peripheral portion (angle of view: $\theta_1$ to $\theta_2$) of the captured image increases as the image height increases.

In general, the wide-angle objective lens 44 has lens characteristics of forming an image by compressing the angle of view according to an increase in the image height. In the electronic magnification processing described above, magnification is performed corresponding to the lens characteristics (compression ratio). Thus, the visibility of the image (image in the vicinity of the maximum angle of view $\theta_2$) of the peripheral portion of the captured image is improved.

FIG. 9 shows a case in which the aspect ratio of the display area of the image display device 14 is 8:5, and the image display device of Wide Quad-XGA (WQXGA) in the example shown in FIG. 5 corresponds to this case.

In the example shown in FIG. 9, the electronic magnification processing unit 81 performs the first electronic magnification processing by making the magnification of the image of the peripheral portion of the captured image larger than the magnification of the image of the central portion of the captured image based on the control information from the processor CPU 61. The image cutting unit 82 cuts out display image data from the image data that has been subjected to electronic magnification processing so that the same aspect ratio as the aspect ratio (8:5) of the display area of the image display device 14 is obtained, and outputs the cut display image data to the mask processing unit 83. Such image processing corresponds to the first image processing of the invention.

The embodiment shown in FIG. 9 is different from the embodiment shown in FIGS. 7 and 8 in terms of the content of the first electronic magnification processing.

That is, in the first electronic magnification processing shown in FIG. 9, when making the magnification of the image (image indicated by oblique lines) of the peripheral portion of the captured image larger than the magnification of the image of the central portion of the captured image, the magnification of the image of the peripheral portion of the captured image is determined so that the image of the peripheral portion of the captured image is included between the outermost periphery of the image of the central portion of the captured image and the left or right end of the display area of the image display device. Thus, the wide screen of the image display device 14 can be used more effectively.

[When the Aspect Ratios are not the Same (when the Display Area has a Vertically Long Aspect Ratio with Respect to a Captured Image)]

Figure 10:
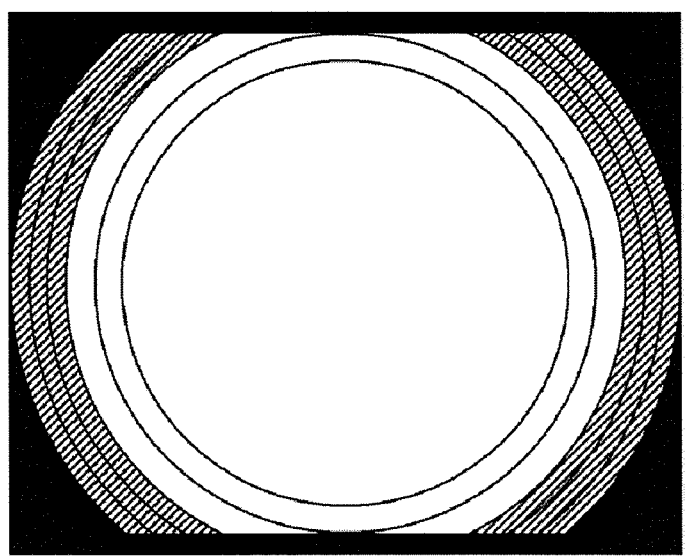
FIG. 10 is a diagram showing an example of the display screen displayed on the image display device in the case where the aspect ratio of a captured image is 4:3 and the aspect ratio of the display area of the image display device is 5:4.

FIG. 10 is a diagram showing an example of a display screen that is displayed on the image display device 14 when the aspect ratio (4:3) of a captured image is not the same as the aspect ratio (5:4) of the display area of the image display device 14. In particular, FIG. 10 shows a case in which the value (1.25) of the aspect ratio of the display area of the image display device 14 is smaller than the value (1.33) of the aspect ratio of the captured image (case in which the display area has a vertically long aspect ratio with respect to the captured image).

In this case, the electronic magnification processing unit 81 performs the second electronic magnification processing in which electronic magnification processing is performed with a fixed magnification for the entire area of the captured image based on the control information from the processor CPU 61, and the image cutting unit 82 outputs image data after the electronic magnification processing to the subsequent mask processing unit 83 as it is.

It is preferable that the magnification of the entire area of the captured image is determined according to the ratio between the number of pixels in the horizontal direction of the display area of the image display device and the number of pixels in the horizontal direction of the captured image. For example, when the captured image has the number of pixels (640×480) of Video Graphics Array (VGA) and the display area of the image display device has the number of pixels (1280×1024) of Super eXtended Graphics Array (SXGA), the magnification of the entire area of the captured image is set to 200% that is the ratio between the number of pixels in the horizontal direction of the captured image and the number of pixels in the horizontal direction of the display area of the image display device.

The mask processing unit 83 performs mask processing on an unnecessary area in the display image data or an area where there is no display image data based on the mask image data of the size corresponding to the number of pixels of the display area of the image display device.

Compared with the mask processing in the case shown in FIG. 6 in which the aspect ratio of the display area of the image display device is the same as the aspect ratio of the captured image, areas corresponding to the upper and lower ends of the display area of the image display device are also subjected to mask processing as shown in FIG. 10, so that display image data corresponding to the display area of the image display device is generated.

Figure 11:
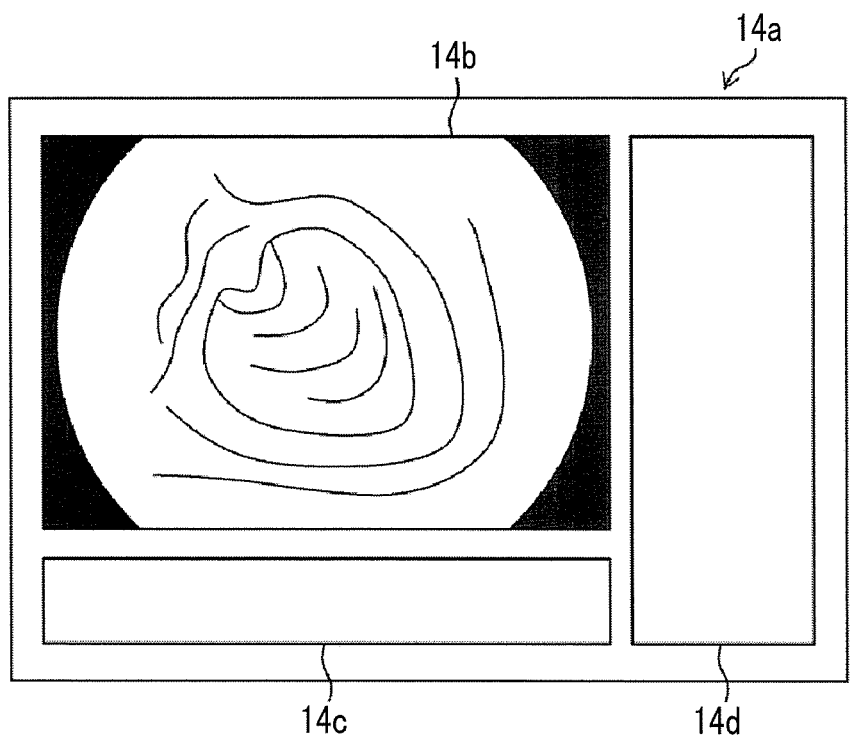
FIG. 11 is a diagram showing an example of the display screen of the image display device.

FIG. 11 is a diagram showing an example of the display screen of the image display device 14.

In the embodiment shown in FIG. 11, a display screen 14a of the image display device 14 has a display area 14b where a captured endoscope image is displayed and information areas 14c and 14d where imaging information, such as patient information, an imaging part, and an imaging date, is displayed as information that comes with the endoscope image.

In the invention, when displaying an endoscope image on the entire surface of the display screen 14a, the display screen 14a is a display area of the image display device 14. When the display screen 14a is a multi-screen having the display area 14b and the information areas 14c and 14d as described above, the display area 14b is a display area of the image display device 14.

In this case, the display size of the display area 14b is not acquired from the image display device 14, but the processor CPU 61 can determine the display size of the display area 14b according to the setting of the multi-screen.

[Example of Application to a Capsule System]

As an electronic endoscope that forms the electronic endoscope system 10 of the invention, a soft endoscope, a hard endoscope, an industrial endoscope, a capsule system (also referred to as a capsule type endoscope), and the like can be used. Hereinafter, a capsule system will be described in detail as an example with reference to the accompanying diagrams.

Figure 12:
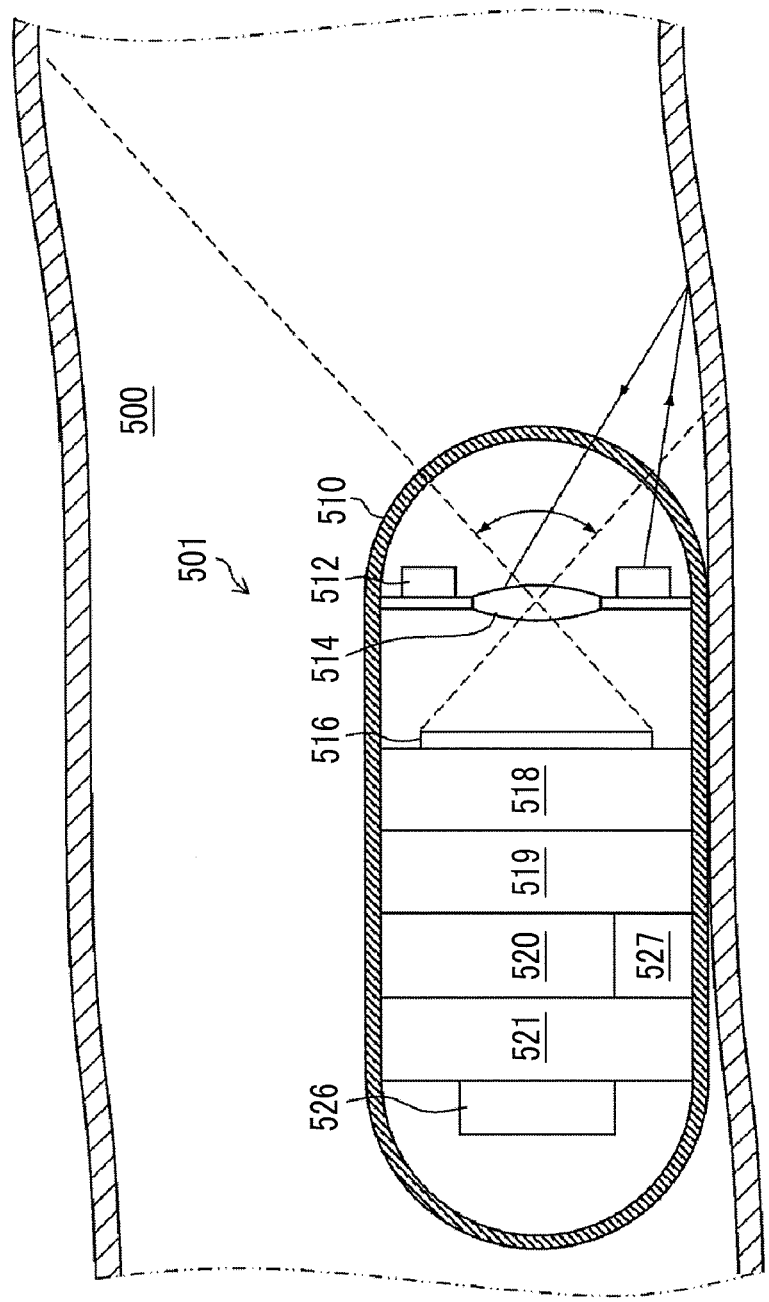
FIG. 12 is a schematic diagram of a capsule system used in an endoscope apparatus of the invention.

As shown in FIG. 12, a capsule system 501 includes an illumination system 512 and a camera including an objective lens 514 and an image sensor 516. An image captured by the image sensor 516 is processed by an image processor 518. The image processor 518 can be implemented by software executed by a digital signal processor (DSP) or a central processing unit (CPU), or by hardware, or by a combination of both software and hardware. The processed image is compressed by an image compression sub-system 519 (may be mounted in software executed by the DSP of the image processor 518 depending on an embodiment). The compressed data is stored in an archive memory system 520. The capsule system 501 includes a battery power supply 521 and an output port 526. The capsule system 501 can move through the gastrointestinal tract (GI tract) 500 by peristalsis.

As the illumination system 512, an LED can be mounted. In FIG. 12, an LED is disposed close to the opening of the camera. However, other arrangements can also be adopted. For example, a light source may be provided behind the opening. Other light sources, such as a laser diode, may also be used. Alternatively, a white light source or a combination of two or more narrow wavelength band light sources can also be used. In order to emit light having a long wavelength, it is possible to use a white LED together with a phosphorescent material that is excited by light of the LED. The white LED may include a blue LED or a purple LED. A predetermined portion of a capsule housing for allowing light to be transmitted therethrough is formed of glass or polymer that is biologically suitable.

The objective lens 514 is for reading an image of a wall of the lumen, such as the GI tract 500, into the image sensor 516, and may include a plurality of refractive lens elements, diffractive lens elements, or reflective lens elements.

The image sensor 516 converts the received light into a corresponding electrical signal, and can be provided as a charge coupled device (CCD) or complementary metal oxide semiconductor (CMOS) type device. The image sensor 516 may be a sensor that responds to a single color, or may include a color filter array that can capture a color image (for example, using RGB or CYM expression). The image sensor 516 corresponds to one form of the solid state imaging device of the invention.

The analog signal from the image sensor 516 is preferably converted into a digital form so as to be able to be processed in a digital format. Such conversion is performed using an analog-to-digital (A/D) converter provided in a sensor (in the case of the present embodiment) or in another portion of a capsule housing 510. The A/D unit can also be provided between the image sensor 516 and another portion of the system. The LED of the illumination system 512 is synchronized with the operation of the image sensor 516. One of the functions of a control module (not shown) of the capsule system 501 is to control the LED during the operation of capturing an image.

An endoscope storage unit 527 stores sensor information of the image sensor 516 and lens information of the objective lens 514 that correspond to the imaging device information 49A and the lens information 49B stored in the endoscope storage unit 49 of the embodiment described above. The sensor information of the image sensor 516 and the lens information of the objective lens 514 that are stored in the endoscope storage unit 527 are transmitted to the processor device through the output port 526.

Figure 13:
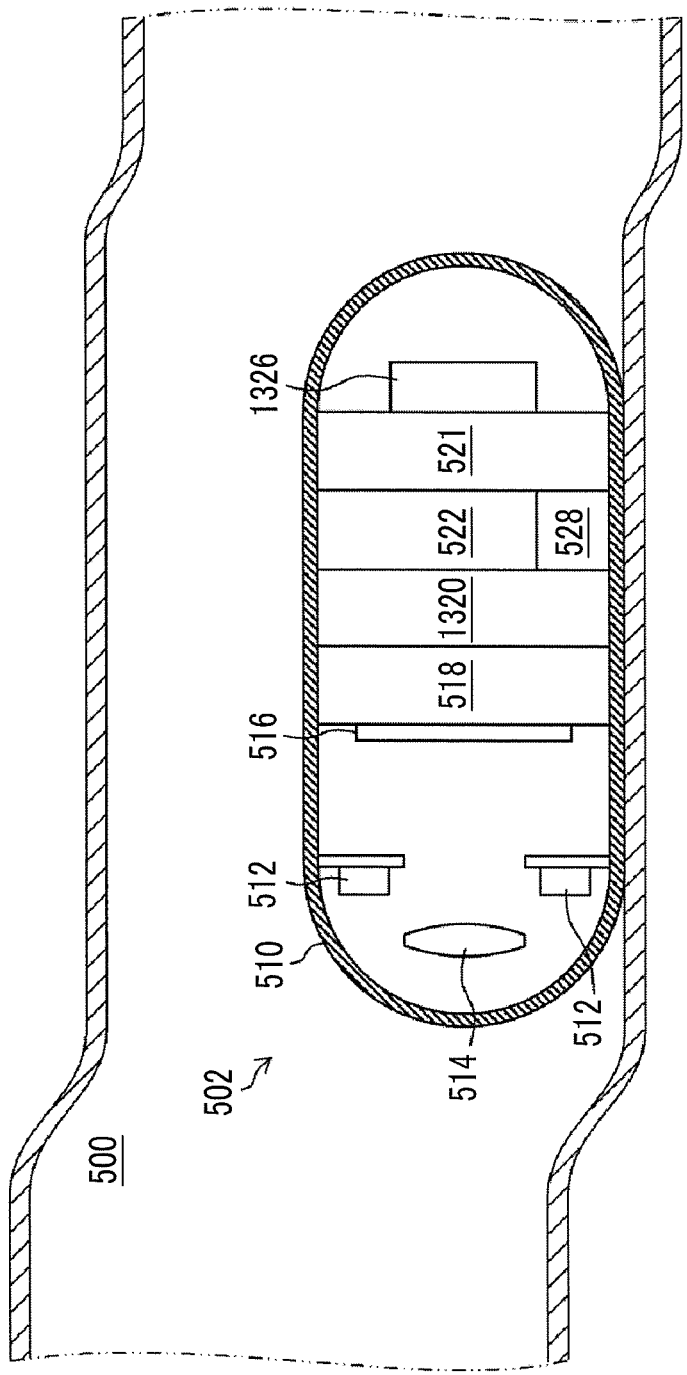
FIG. 13 is a schematic diagram of a capsule system of another embodiment.

FIG. 13 shows a swallowable type capsule system 502 according to an embodiment of the invention. The capsule system 502 can be made to have substantially the same configuration as the capsule system 501 shown in FIG. 12 except that the archive memory system 520 and the output port 526 are not required. The capsule system 502 also includes a communication protocol encoder 1320 and a transmitter 1326 that are used for wireless transmission. Among the elements of the capsule system 501 and the capsule system 502, substantially the same elements are denoted by the same reference numerals. Accordingly, the structures and functions of the elements will not be described again herein. A control module 522 performs overall control of the capsule system 502. The communication protocol encoder 1320 is implemented by software executed by the DSP or the CPU, or by hardware, or by a combination of both software and hardware. The transmitter 1326 includes an antenna system for transmitting a captured digital image.

A part of a ROM (not shown) of the control module 522 functions as an endoscope storage unit 528. The endoscope storage unit 528 stores sensor information and lens information corresponding to the imaging device information 49A and the lens information 49B that are stored in the endoscope storage unit 49 of the embodiment described above. The sensor information and the lens information stored in the endoscope storage unit 528 are transmitted to the processor device through the transmitter 1326.

The processor device corresponding to each of the capsule systems 501 and 502 has basically the same configuration as the processor device of the embodiment described above except that the processor device corresponds to the capsule system, and performs the first image processing and the second image processing. Therefore, the same effect as the effect described in the above embodiment is obtained.

Other Embodiments

The magnification of a central portion and a peripheral portion of a captured image in the first image processing of the image processing unit 65 (electronic magnification processing unit 81) may be arbitrarily set by the user using the magnification setting unit 51 as shown in FIG. 4.

In this case, the setting of the magnification by the magnification setting unit 51 may be performed by arbitrarily setting the display size of the central portion of the captured image, or may be performed by arbitrarily setting the display size of the peripheral portion of the captured image.

That is, the processor CPU 61 (display size acquisition unit) can acquire the display size of the display area of the image display device 14 through communication with the image display device 14. When the display size of the central portion of the captured image is arbitrarily set, the magnification setting unit 51 can calculate the display size of the peripheral portion of the captured image from the display size of the central portion of the captured image set arbitrarily and the display size of the display area acquired by the processor CPU 61, and can set the magnification of the central portion and the peripheral portion of the captured image from the display size of the central portion set arbitrarily and the calculated display size of the peripheral portion.

Similarly, when the display size of the peripheral portion of the captured image is arbitrarily set, the magnification setting unit 51 can calculate the display size of the central portion of the captured image from the display size of the peripheral portion of the captured image set arbitrarily and the display size of the display area acquired by the processor CPU 61, and can set the magnification of the central portion and the peripheral portion of the captured image from the display size of the peripheral portion set arbitrarily and the calculated display size of the central portion.

According to the aspect ratio of the display area of the image display device and the aspect ratio of the captured image, the image processing unit 65 of the present embodiment performs the first image processing for making the magnification of the image of the peripheral portion of the captured image larger than the magnification of the image of the central portion of the captured image so as to match the aspect ratio of the display area of the image display device in the case where the value of the aspect ratio of the display area of the image display device is larger than the value of the aspect ratio of the captured image, and performs the second image processing for fixing the magnification of the entire area of the captured image so as to match the aspect ratio of the display area of the image display device in the case where the value of the aspect ratio of the display area of the image display device is equal to or less than the value of the aspect ratio of the captured image. However, the invention is not limited to this, and the mode selection unit 53 (refer to FIG. 4) that selects a first mode, in which the image processing unit 65 performs the first image processing, or a second mode, in which the image processing unit 65 performs the second image processing, by manual operation, may be selected, and the image processing unit 65 may perform the image processing by giving priority to the first image processing in the case where the first mode is selected by the mode selection unit 53 and perform the image processing by giving priority to the second image processing in the case where the second mode is selected by the mode selection unit 53. According to the above, by giving priority to image processing in the first or second mode by manual operation, it is possible to meet a demand to see an original image even if the image of the peripheral portion is compressed or a demand to give priority to the visibility of the peripheral portion even if the visibility of the central portion is degraded.

In addition, the processor CPU 61 (lens information acquisition unit) can acquire the lens information 49B indicating the lens characteristics of the objective lens 44 from the electronic endoscope 11 through communication with the electronic endoscope 11. In addition, the lens information 49B can include the maximum angle of view ($\theta_2$) of the objective lens 44, the angle of view ($\theta_1$) of the central portion of the captured image, the compression rate of the image of the peripheral portion of the captured image, and the like.

The image processing unit 65 can perform only the second image processing when the maximum angle of view ($\theta_2$) of the objective lens 44 of the electronic endoscope 11 is determined to be less than 120° based on the lens information 49B acquired by the processor CPU 61. When the objective lens 44 of the electronic endoscope 11 is determined to be a wide-angle lens having the maximum angle of view ($\theta_2$) of 120° or more based on the lens information 49B acquired by the processor CPU 61, the image processing unit 65 can switchably perform the first image processing or the second image processing according to the aspect ratio of the display area of the image display device, and the aspect ratio of the captured image.

If the maximum angle of view ($\theta_2$) of the objective lens 44 and the angle of view ($\theta_1$) of the image of the central portion of the captured image can be acquired from the lens information 49B, the image processing unit 65 can specify the image of the central portion and the image of the peripheral portion of the captured image when making the magnification of the image of the peripheral portion of the captured image larger than the magnification of the image of the central portion.

When the processor CPU 61 (display information acquisition unit) cannot acquire information regarding the aspect ratio of the display area of the image display device (an aspect ratio, a value indicating the aspect ratio, or the number of pixels in the horizontal and vertical directions), it is preferable that the image processing unit 65 performs only the second image processing for fixing the magnification of the entire area of the captured image without performing the first image processing.

It is needless to say that the invention is not limited to the embodiments described above and various modifications can be made within the scope and spirit of the invention.

What is claimed is:

1. An image processing apparatus for an electronic endoscope, comprising:
    an image display device;
    a processor device, configured to:
        receive an imaging signal captured by an electronic endoscope is input;
        perform image processing on the imaging signal input from the input unit;
        output an imaging signal, which has been subjected to the image processing to the image display device,
    wherein the processor device performs first image processing in the case where a value of an aspect ratio of a display area of the image display device is larger than a value of an aspect ratio of a captured image indicated by the imaging signal, and performs second image processing in the case where the value of the aspect ratio of the display area of the image display device is equal to or less than the value of the aspect ratio of the captured image indicated by the imaging signal, and the first image processing is for making a magnification of an image of a peripheral portion outside a central portion of the captured image larger than a magnification of an image of the central portion so as to match the aspect ratio of the display area of the image display device, and the second image processing is for fixing a magnification of an entire area of the captured image so as to match the aspect ratio of the display area of the image display device.

2. The image processing apparatus for an electronic endoscope according to claim 1,
wherein the processor device further acquires lens information indicating lens characteristics of an objective lens from the electronic endoscope through communication with the electronic endoscope,
wherein the processor device performs only the second image processing in the case where it is determined that a maximum angle of view of the objective lens of the electronic endoscope is less than 120° based on the lens information.

3. The image processing apparatus for an electronic endoscope according to claim 1,
wherein the processor device further acquires lens information indicating lens characteristics of an objective lens from the electronic endoscope through communication with the electronic endoscope,
wherein, in the case where the value of the aspect ratio of the display area of the image display device is larger than the value of the aspect ratio of the captured image indicated by the imaging signal and the objective lens of the electronic endoscope is determined to be a wide-angle lens, which has a maximum angle of view of 120° or more and which forms an image by compressing an angle of view according to an increase in an image height of the captured image, based on the lens information, the processor device makes the magnification of the image of the peripheral portion larger than the magnification of the image of the central portion by setting the image having a compressed angle of view as the image of the peripheral portion.

4. The image processing apparatus for an electronic endoscope according to claim 1,
wherein the processor device further acquires lens information indicating lens characteristics of an objective lens from the electronic endoscope through communication with the electronic endoscope,
wherein, in the case of making the magnification of the image of the peripheral portion of the captured image larger than the magnification of the image of the central portion, the processor device specifies the image of the central portion and the image of the peripheral portion of the captured image based on the lens information.

5. The image processing apparatus for an electronic endoscope according to claim 3,
wherein the processor device further acquires lens information indicating lens characteristics of an objective lens from the electronic endoscope through communication with the electronic endoscope,
wherein, in the case of making the magnification of the image of the peripheral portion of the captured image larger than the magnification of the image of the central portion, the processor device specifies the image of the central portion and the image of the peripheral portion of the captured image based on the lens information.

6. The image processing apparatus for an electronic endoscope according to claim 1,
wherein processor device further arbitrarily sets the magnification of each of the central portion and the peripheral portion of the captured image in the first image processing of the processor device.

7. The image processing apparatus for an electronic endoscope according to claim 2,
wherein the processor device further arbitrarily sets the magnification of each of the central portion and the peripheral portion of the captured image in the first image processing of the processor device.

8. The image processing apparatus for an electronic endoscope according to claim 3,
wherein the processor device further arbitrarily sets the magnification of each of the central portion and the peripheral portion of the captured image in the first image processing of the processor device.

9. The image processing apparatus for an electronic endoscope according to claim 4,
wherein the processor device further arbitrarily sets the magnification of each of the central portion and the peripheral portion of the captured image in the first image processing of the processor device.

10. The image processing apparatus for an electronic endoscope according to claim 5,
wherein the processor device further arbitrarily sets the magnification of each of the central portion and the peripheral portion of the captured image in the first image processing of the processor device.

11. The image processing apparatus for an electronic endoscope according to claim 6,
wherein the processor device further acquires a display size of a display area of the image processing apparatus through communication with the image display device,
wherein the processor device sets the magnification of each of the central portion and the peripheral portion of the captured image based on the display size of the display area of the image processing apparatus and a set display size of the central portion of the captured image by arbitrarily setting the display size of the central portion of the captured image.

12. The image processing apparatus for an electronic endoscope according to claim 7,
the processor device further acquires a display size of a display area of the image processing apparatus through communication with the image display device,
wherein the processor device sets the magnification of each of the central portion and the peripheral portion of the captured image based on the display size of the display area of the image processing apparatus and a set display size of the central portion of the captured image by arbitrarily setting the display size of the central portion of the captured image.

13. The image processing apparatus for an electronic endoscope according to claim 8,
wherein the processor device further acquires a display size of a display area of the image processing apparatus through communication with the image display device,
wherein the processor device sets the magnification of each of the central portion and the peripheral portion of the captured image based on the display size of the display area of the image processing apparatus and a set display size of the central portion of the captured image by arbitrarily setting the display size of the central portion of the captured image.

14. The image processing apparatus for an electronic endoscope according to claim 6,
wherein the processor device further acquires a display size of a display area of the image processing apparatus through communication with the image display device,
wherein the processor device sets the magnification of each of the central portion and the peripheral portion of the captured image based on the display size of the display area of the image processing apparatus and a set display size of the peripheral portion of the captured image by arbitrarily setting the display size of the peripheral portion of the captured image.

15. The image processing apparatus for an electronic endoscope according to claim 1,
wherein the processor device further acquires information regarding the aspect ratio of the captured image through communication with the electronic endoscope.

16. The image processing apparatus for an electronic endoscope according to claim 1,
wherein the processor device further acquires information regarding the aspect ratio of the display area of the image display device through communication with the image display device.

17. The image processing apparatus for an electronic endoscope according to claim 16,
wherein the processor device performs the second image processing in the case where the information regarding the aspect ratio of the display area of the image display device is not able to be acquired.

18. The image processing apparatus for an electronic endoscope according to claim 1,
wherein the processor device further selects a first mode in which the first image processing is performed, or a second mode in which the second image processing is performed, by manual operation,
wherein the processor device performs the image processing by giving priority to the first image processing in the case where the first mode is selected, and performs the image processing by giving priority to the second image processing in the case where the second mode is selected.

19. An electronic endoscope system, comprising:
an electronic endoscope;
the image processing apparatus for an electronic endoscope according to claim 1 to which an imaging signal captured by the electronic endoscope is input; and
an image display device to which the imaging signal after image processing from the image processing apparatus is input.

20. An image processing method, applicable to an image processing apparatus, comprising:
receiving an imaging signal captured by an electronic endoscope;
performing image processing on the input imaging signal; and
outputting an imaging signal after the image processing to an image display device,
wherein, first image processing is performed in the case where a value of an aspect ratio of a display area of the image display device is larger than a value of an aspect ratio of a captured image indicated by the imaging signal, and second image processing is performed in the case where the value of the aspect ratio of the display area of the image display device is equal to or less than the value of the aspect ratio of the captured image indicated by the imaging signal, and
the first image processing is for making a magnification of an image of a peripheral portion outside a central portion of the captured image larger than a magnification of an image of the central portion so as to match the aspect ratio of the display area of the image display device, and the second image processing is for fixing a magnification of an entire area of the captured image so as to match the aspect ratio of the display area of the image display device.

* * * * *